United States Patent [19]

Shurben

[11] Patent Number: 4,960,565

[45] Date of Patent: Oct. 2, 1990

[54] ACID MONITORING KIT

[75] Inventor: William S. Shurben, Kanata, Canada

[73] Assignee: Ecostix Environmental Inc., Ontario, Canada

[21] Appl. No.: 322,987

[22] Filed: Mar. 14, 1989

[51] Int. Cl.$^5$ ............................................. G01N 33/18
[52] U.S. Cl. ....................................... 422/61; 422/56; 422/57; 436/163; 436/810
[58] Field of Search ........................ 423/55, 56, 57, 61, 423/58; 436/125, 163, 810; 210/749, 169, 514, 515, 96.1; D10/104

[56] References Cited

U.S. PATENT DOCUMENTS

| | | | |
|---|---|---|---|
| 4,108,729 | 8/1978 | Mennen | 422/56 |
| 4,486,536 | 12/1984 | Baker et al. | 422/61 |
| 4,523,852 | 6/1985 | Bauer | 422/55 |
| 4,654,309 | 3/1987 | Mlinar et al. | 436/20 |

Primary Examiner—Christine M. Nucker
Assistant Examiner—Gregory R. Muir
Attorney, Agent, or Firm—Nixon & Vanderhye

[57] ABSTRACT

An acid monitoring kit is provided which is especially useful for monitoring acid rain. The kit includes a base plate having three discrete areas. One area is provided with a plurality of discrete separable bibulous pH indicator strips, each strip being impregnated with a selected acid-base indicator which is visually recognizable as at least one unique color in each such bibulous pH indicator strip when the bibulous strip is dry, and as a different color upon being wetted with water, the different color being dependent on the pH of the water. A second discrete area is provided with a plurality of color comparison reference standards in a plurality of zones, each zone being of a unique color which corresponds to the color of the water-wetted bibulous pH indictor strip, whereby comparison of the unique color of the pH indicator strip with the unique color of the reference standard provides an indication of the pH of the water. A third discrete area is also labelled to provide the requisite information for the use of such acid monitoring kit to correlate the unique color developed in the bibulous pH indicator strip to a unique color of the reference standard to provide an indication of the pH of the water.

15 Claims, 1 Drawing Sheet

ACID MONITORING KIT

BACKGROUND OF THE INVENTION (a) Field of the Invention

This invention relates to a pH monitoring kit. In particular it is directed to such pH monitoring kit for the monitoring of "acid rain" and for the determination of the pH of rivers and lakes to ascertain which species of fish can survive in such rivers and lakes.

Acidic compounds contain hydrogen ions when dissolved in solution. The stronger the acid, the more hydrogen ions it contains. The more ions, the more destructive the acid. Acidity is measured on the pH scale which runs from 1 to 14. The scale is logarithmic; one pH unit represents a factor of 10 hydrogen ions. Thus, pH 5 solutions contain 10 times more hydrogen ions than pH 6 solutions, 100 times more hydrogen ions than pH 7 solutions, and so on.

Normal rain has a pH in the range of 5.6 to as low as 2.0, which is slightly acidic because carbon dioxide present in the atmosphere forms carbonic acid in the rainwater. Acid rain is about 30 to 300 times more acidic than "normal" rain, ranging from pH 4.5 to as low as pH 2.0.

Acid rain may vary qualitatively from place to place and time to time. Present day rains contain nitric acid plus sulphuric acid in changing proportions. Nitric acid forms in the atmosphere from water vapour plus nitrous oxides ($NO_x$), which are common components of automobile exhaust. Sulphuric acid starts out in coal. Sulphur released during coal combustion becomes sulphur dioxide ($SO_2$) and other sulphur oxides. The addition of water in rain results in the production of sulphuric acid.

Before sulphur oxides and nitrous oxides fall to the ground as acid rain, they can stay in the atmosphere for up to five days. Dead lakes are the most traceable victims of acid rain. Lakes all over the world are dead or dying, particularly where soils are thin and the bedrock is granite. Vulnerable areas include Scandinavia (30,000 acid lakes), the Canadian Shield (14,000 dead lakes, 300,000 to 600,000 lakes at risk), the New York Adirondacks (200 dead lakes, thousands dying) plus mountain lakes in Colorado and California.

Acid rain also attacks trees from several flanks; it damages the tree directly, the leaves being the prime targets; indirectly it upsets the balance of soil nutrients necessary for tree growth.

In Sweden, one spruce tree in four and one pine tree in seven are losing needles at an alarming rate. Throughout Europe 7 million hectares of forest—an area roughly the size of England—have been damages by acid rain and by other pollutants. In Canada and the United States the entire maple syrup industry, which depends on healthy sugar maples, is at risk.

Acid rain compromises the health of plants and animals, including humans. It promotes or prolongs chest colds, stuffy noses, bronchitis, allergies—maybe even lung cancer.

The United Nations Environment Programme estimates 600 million city dwellers worldwide are at risk from its effects.

Acid rain poisons fish and the animals that eat them. It speeds up heavy metal leaching from soils and pipelines. Toxic metals accumulate in animal tissues and drinking water, climbing higher and higher up the food chain.

Even buildings, roads and other human creations are not safe. Acid rain speeds up building deterioration 100 times.

Acid rain exacts tremendous costs. Tourism, agriculture, fisheries, forestry, construction and health care are all effected. Accordingly, it is exceedingly desirable to monitor acid rain.

(b) Description of the Prior Art

Many patents have issued which are directed to acid indicators which may be used to monitor acid rain. For example, Canadian Patent Number No. 735,807 patented June 7, 1966 by B.J. Eiseman Jr. provided acid-base test papers or other cellulosic materials.

Canadian Patent Number No. 686,024 patented May 5, 1964 by G.F. Collins provided test units in dry form, in which a bibulous carrier, e.g., absorbent paper, was impregnated with a pH indicator which provided a colorimetric indication of hydrogen ion concentration.

Canadian Patent Number No. 712,088 patented June 22, 1965 by John Rebar, Jr. et al provided a pH test portion of a "dip and read" type of indicator test strip.

Canadian Patent Number No. 1,186,202 issued Apr. 30, 1983 to M. Blumenthal, and its corresponding U.S. Pat. No. 4,349,353 patented Sept. 14, 1982 provided a test kit for determining the amount of soaps or other alkaline substances in fat. The test kit comprised a test solution and a set of standardized colors. The test solution comprised a pH indicator dye having a visible color change in the pH range of from 2.5 to 7.0 and a solvent in which the dye was soluble and with which the fat was immiscible. The dye and solvent were present in the test solution in amounts effective to provide a visible color change which depended upon the amount of alkaline substances, e.g., soaps, in the fat. The pH of the test solution was such that the color of the test solution prior to the mixing step corresponded to the color of the dye at the lower end of the color change range for the dye. After mixing, the fat and test solution were allowed to separate into a solvent phase and a fat phase. The amount of alkaline substances in the fat was then determined from the color developed in the solvent phase by comparing the developed color to a known standard, e.g., visually, in a coorimeter or in a spectrophotometer. The test of colors was standardized so that each color corresponded to a color developed when a predetermined amount of test solution was mixed with a predetermined amount of fat containing a specified amount of alkaline substances. The kit could also contain other apparatus for performing the method, e.g., test tubes, dispensing bottles, caps for the test tubes, droppers, ladles, test tube holders, etc.

SUMMARY OF THE INVENTION (a) Aims of the Invention

Thus, the prior art attempted to solve the problem of providing a simple, convenient, rapid and dependable acid monitoring system by improving the actual chemicals used as the pH indicator or by improving the bibulous material upon which the chemicals were absorbed or by providing an improved color comparison reference standard. No steps have heretofore been taken to provide a more simple, convenient and dependable acid monitoring kit, and the provision of such kit is the principal object of this invention.

(b) Statement of Invention

By a broad aspect of this invention, an acid monitoring kit is provided comprising a base having (1) one discrete area provided with a plurality of discrete, separable, bibulous, pH indicator strips, each strip being impregnated with at least one selected acid-base indicator, the acid-base indicator being visually recognizable as at least one unique color on each bibulous pH indicator strip when the bibulous strip is dry, and as a different color upon being wetted with water, the different color being dependent on the pH of the water; (ii) a second discrete area provided with a plurality of color comparison reference standards in a plurality of zones, each zone being of a unique color which corresponds to the color of the water-wetted, bibulous pH indictor strip, whereby comparison of the unique color of the pH indicator strip with the unique color of the reference standard provides an indication of the pH of the water; and (iii) a third discrete area labelled to provide equisite information for the use of the acid monitoring kit, to correlate the unique color developed in the bibulous pH indicator strip to a unique color of the reference standard to provide an indication of the pH of the water.

This invention also provides an acid monitoring kit formed of a cardboard base plate including two discrete areas in the form of two panels hingedly connected in seriatim to one another by way of a connecting panel, wherein: a first discrete area (i) is provided with a plurality of discrete, separable, bibulous, pH indicator strips, each strip comprising a non-bleeding rectangular strip, and being impregnated with two selected acid-base indicators, to provide two unique, visually-recognizable areas and a zone thereon which may be gripped by the fingers of the user the acid-base indicator being visually-recognizable as at least one unique color on each bibulous pH indicator strip when the bibulous strip is dry, and as a different color upon being wetted with water, the different color being the pH of the water; a second discrete area (ii) is provided with seven distinct rectangular areas, each area including two unique different colors to provide a plurality of color comparison reference standards in a plurality of zones, each zone being of a unique color which corresponds to the color of the water-wetted bibulous pH indicator strip, whereby comparison of the unique color of the pH indicator strip with the unique color of the reference standard provides an indication of the pH of the water, and, by reference to indicia proved thereon to indicate which fish are unlikely to be found in the water which wetted the bibulous strip; and a third discrete area (iii) is on the back face of the first discrete panel, the back face being imprinted with instructions for the use of the acid monitoring kit to correlate the unique color developed in the bibulous pH indicator strip to a unique color on the reference standard, to provide an indication of the pH of the water.

This invention still further provides a kit adapted to assist in the determination of the likely presence of aquatic species in a body of water in dependence upon a determined pH for the body of water, the kit comprising in combination: first and second base members hingedly connected to one another so as to be relatively foldable between closed and opened conditions; a plurality of discrete, separable, bibulous, pH indicator strips attached to the first base member so as to be covered by the second base member when the first and second base members are in the closed condition thereof, and being exposed when the first and second members are in the opened condition thereof so as to allow a user to separate at least one of the indicator strips from the first member; each indicator strip being provided with a pH test region which consists essentially of an acid-base indicator which changes from a normal, visually-perceptible color when dry to a visually-perceptible unique different color when wetted with water from the body of water being tested, wherein the unique color is indicative of the pH of the body of water being tested; a plurality of color comparison reference standards imprinted upon the second member, each color comparison reference standard corresponding to one possible pH indicative unique color of the wetted indicator strip; and a plurality of information zones each being associated with a respective one of the color comparison reference standards for identifying the likely presence of aquatic species in the body of water being tested in dependence upon the pH of the body of water corresponding to the respective color comparison reference standard, whereby matching the unique color of the water-wetted indicator strip with one of the color comparison reference standards will allow a user to determine the likely presence of aquatic species in the body of water by virtue of the associated information zones.

(c) Other Features of the Invention

In other words the kit includes a base plate formed of cardboard, the base plate including two discrete areas in the form of panels hingedly-connected in seriatim to one another through an intermediate panel.

Preferably, the above-mentioned area which is labelled to provide the requisite information for the use of the acid monitoring kit is a third area which on the rear face of the first discrete area of the rear face of the second discrete area, that face being imprinted with instructions for the use of the acid monitoring kit to correlate the unique color developed in the bibulous pH indicator strip to a unique color of the reference standard to provide an indication of the pH of said water.

The bibulous strip may have two, three or four distinct different colored visually-recognizable areas, and preferably includes non-impregnated areas which may be gripped by the fingers of the user.

The color comparison standard may comprise up to fourteen columns, each column including up to four distinct, differently colored visually-recognizable areas, or it may comprise six columns, each column having at least two different distinct differently-colored, visually-recognizable, areas representative of increasing acidity, and also including indicia indicative of which fish are unlikely to survive at the pH represented by the unique color, and also including indicia indicative of which fish cannot survive at the designated pH.

Acid-base indicators which may be used in the bibulous pH indicator strips, which are preferably formed of a cellulosic material e.g., non-bleeding rectangular strips and which form an essential part of the pH monitor kit of an aspect of this invention, are organic dyes which change color with a change in the concentration of hydrogen ion. Usually these dyes contain either basic groups, e.g., amino groups, or acidic groups which can react with the acid or base present. Some typical examples of such dyes which are used are: Congo Red, Brilliant Yellow, Litmus, Neutral Red, Bromophenol Red, Phenol Red, Thymol Blue, Methyl Red and the like.

One commercially-available example of such indicator strips are those sold under the Trade Mark COLORPHAST by E. Merck in Darmstadt, Germany. These pH indicator strips will register in the pH range of 2.0 to 7.0. The bibulous strip in such case will have only two distinctly differently colored zones.

Another commercially-available example of such indicator strips are the non-bleeding pH sticks sold by Brinkmann Instruments (Canada) Ltd. and known by the Trade Mark MACHEREY-NAGEL. In contrast to conventional indicator papers, the indicator dyes of such pH sticks are substantively bound to the cellulose fibres. As a result the possibility of the color bleeding, even in strongly basic solutions, is avoided. Furthermore the use of such pH sticks provides the following advantages: (1) measurement of pH value is possible even in unbuffered or very weakly buffered solutions, since the sticks can be left in the solution until the final color change is completed; (2) test samples are not contaminated by the indicator dyes; (3) colors of the individual color fields cannot run into each other, thereby allowing a more precise comparison with the color scale; (4) the indicator dyes guarantee a sharp differentiation between the individual pH values and a clear and easy comparison to the color scale; and (5) the application is simple, and the strips are sufficiently long to avoid contact between the fingers and the test sample.

Figure 1:
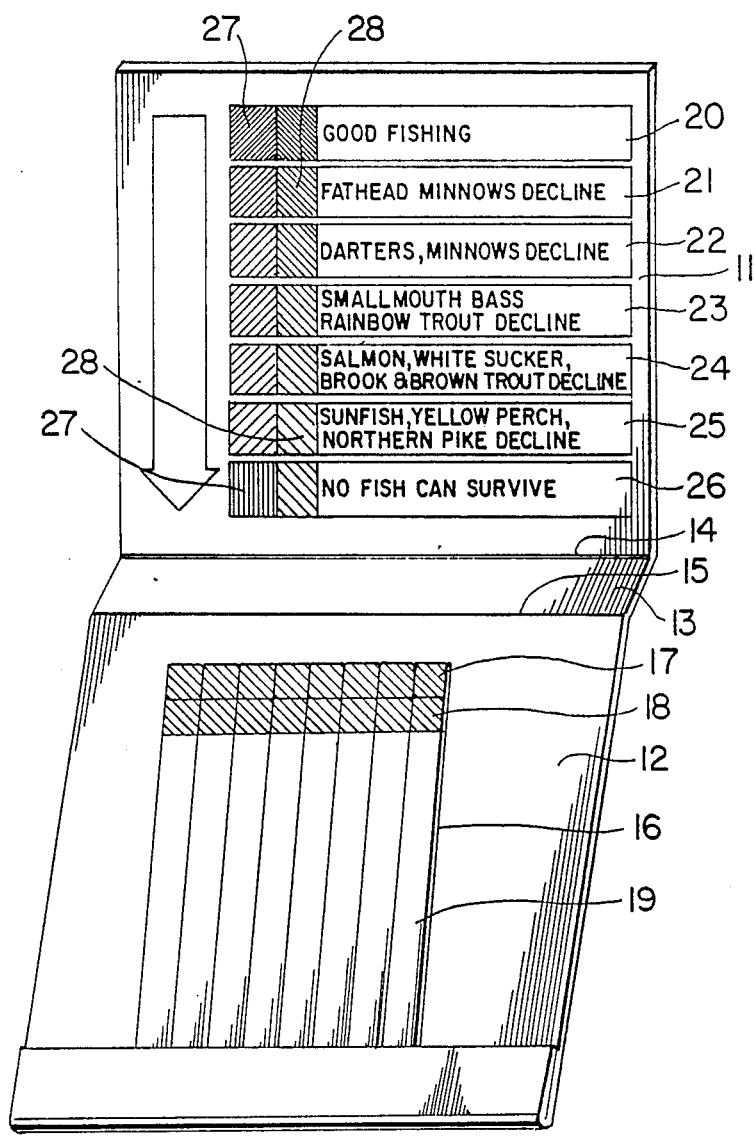
FIG. 1 of the accompanying drawing is a perspective view showing a preferred embodiment of the invention which is commercially identified by the applicant by the Trademark FISH STICKS.

As seen in the accompanying drawing FIGURE, a preferred embodiment of this invention 10 includes two discrete areas, namely, first panel 11, and second panel 12, joined by a connecting panel 13, i.e. panels 11, 12 and 13 are hingedly joined together in seriatim, e.g. by fold line 14 between panels 11 and 13, and by fold line 15 between panels 13 and 12.

The second panel 12 is provided with plural, e.g. six, separable, bibulous pH strips 16, each provided with two indicator dyes impregnated into the ends thereof to provide two unique, differently colored, visually recognizable, areas 17, 18 and a non-impregnated, finger-gripping area 19. These strips 16 are non-bleeding pH sticks in which the indicator dyes are substantively bound to the cellulosic fibres forming the sticks.

The interconnecting panel 13 interconnects the first panel 11 with the second panel 12. The first panel 11 includes seven horizontal areas 20, 21, 22, 23, 24, 25 and 26 each of which comprise color comparison reference standard, having two unique, different, visually-recognizable, colors 27, 28. Areas 20–26 are displayed in order of increasing acidity and are labelled to indicate were the fish are not likely to survive.

Panel 11 adapted to be folded over panel 12, in the nature of a cover, as shown by the broken arcuate line. The reverse face of the panel 11 includes imprinted instructions for the use of the pH indicator kit, e.g.

1. Tear off a pH indicator strip;
2. Dip the stick into the body of water;
3. Match the color of the pH indicator strip against the color reference standard in the second discrete area;
4. These colors indicate which fish are unlikely to be found in the body of water.

DESCRIPTION OF PREFERRED EMBODIMENTS

In one use of this pH monitor kit of an aspect of this invention, the pH of a lake can be monitored. At pH 6.8, a pH of a lively robust lake exists which is the home for a healthy animal population, i.e., fish, crustaceans, molluscs, insects, snakes, turtles, birds and mammals. At pH 6.1 bacteria, green algae, zooplankton and insects flourish and brown algae becomes scarce. At pH 5.8, fewer lake trout embryos survive. Sensitive crustaceans disappear. At pH 5.6, opossum shrimp, the prime food source for lake trout, disappear. Lake trout and white suckers decline. Algae mats appear along the shoreline. Plant production increases under water. At pH 5.4, parasites infest crayfish. Hardier crustaceans expire. Lake trout are sterile. Birds leave for other feeding grounds. At pH 5.1, white suckers cease reproduction. At pH 4.9, crayfish, clams, mayflies, dragonflies disappear. Loons, mink, remaining birds abandon lake. Yellow perch and lake chub the last survivors. At pH 4.7, no birds, fish, amphibians or mammals exist. Finally, at pU 4.3, a crystal clear, blue- green lake exists which supports no life.

As a specific example, using the monitor kit 10 shown in the accompanying drawing (which, as indicated above, is commercially identified by the applicant by the Trademark FISH STICKS), the likely presence of fish in a body of water may be determined, since the monitor kit includes a plurality of color comparison reference standards, whose colors are displayed in order of increasing acidity and are labelled to indicate where fish do not survive. The color standards may be, e.g., as follows: (1) Lake Ontario; (2) Fathead Minnows; (3) Darters, Minnows; (4) Smallmouth Bass, Rainbow Trout, Roach; (5) Atlantic Salmon, Lake Trout, White Sucker, Brook Trout, Brown Trout; and (6) Sunfish, Yellow Perch. No surviving fish above this level.

In use, indicator strip 16 of the monitor kit 10 shown in the accompanying drawing FIGURE is dipped in a lake, river or stream. The moistened test zone is compared with the color chart. The chart indicates the species of fish at risk.

Another embodiment of the present invention is identified by the applicant by the Trade Mark THE ARK PROJECT which includes the color comparison reference standards calibrated in pH and a plurality of narrow range pH indicator strips. To monitor a lake, river, pond or other body of water, dip the strip colored side down into the water. The color of the moistened pH strip is matched against the color chart. A reading below pH 5.6 means acidification has begun. Readings from pH 5.6 to 6.5 and higher indicate little risk from acid rain.

To monitor a rainstorm, snowstorm or fog, precipitation may be collected in a clean non-metallic container. The strips should be left in rainwater for up to fifteen minutes. Readings below pH 5.6 indicate acid pollution.

CONCLUSION

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be within the full range of equivalence of the following claims.

What I claim is:
1. An acid monitoring kit comprising:
   a base having;
   (i) one discrete area provided with a plurality of discrete separable, bibulous, pH indicator strips, each strip being impregnated with at least one selected acid-base indicator, said acid-base indi- cator being visually recognizable as at least one unique color on each said bibulous pH indicator strip when said bibulous strip is dry, and as a different color upon being wetted with water, said different color being dependent on the pH of said water;

(ii) a second discrete area provided with a plurality of color comparison reference standards in a plurality of zones, each zone being of a unique color which corresponds to the color of said water-wetted, bibulous pH indicator strip, whereby comparison of the unique color of said pH indicator strip with the unique color of said reference standard provides an indication of the pH of said water; and (iii) a third discrete area labelled to provide requisite information for the use of said acid monitoring kit, to correlate the unique color developed in said bibulous pH indicator strip to a unique color of said reference standard to provide an indication of the pH of the water.

2. The acid monitoring kit of claim 1 wherein said bibulous strips are non-bleeding rectangular strips.

3. The acid monitoring kit of claim 1, wherein said base comprises a base plate formed of cardboard, said base plate including two said discrete areas in the form of panels hingedly-connected in seriatim to one another through an intermediate panel.

4. The acid monitoring kit of claim 3, wherein said third discrete area comprises an area on the rear face of said first discrete area or on the rear face of said second discrete area, said face being imprinted with instructions for the use of said acid monitoring kit to correlate the unique color developed in said bibulous pH indicator strip to a unique color of said reference standard to provide an indication of the pH of said water.

5. The acid monitoring kit of claim 1, wherein said bibulous strips are of a cellulosic material.

6. The acid monitoring kit of claim 2, wherein said acid-base indicator is an organic dye selected from the group consisting of Congo Red, Brilliant Yellow, Litmus, Neutral Red, Bromophenol Red, Phenol Red, Thymol Blue, or Methyl Red.

7. The acid monitoring kit of claim 6, wherein each of said bibulous strips has two, distinct unique differently-colored visually-recognizable areas.

8. The acid monitoring kit of claim 2, including a zone on each said bibulous strip which may be gripped by the fingers of the user.

9. The acid monitoring kit of claim 1, wherein said color comparison standard comprises fourteen columns, each column including four distinct, unique, differently-colored, visually-recognizable areas.

10. The acid monitoring kit of claim 1, wherein said color comparison standard comprises six columns, each column; having at least two distinct, unique, differently-colored visible, visually recognizable areas representative of increasing acidity, and also including indicia indicative of which fish cannot are unlikely to survive at the designated pH represented by said unique color.

11. The acid monitoring kit of claim 6, wherein each of said bibulous strips has three distinct, unique, differently-colored, visually-recognizable areas.

12. The acid monitoring kit of claim 6, wherein each of said bibulous strips has four distinct, unique, different colored, visually-recognizable areas.

13. An acid monitoring kit formed of a cardboard base plate including two discrete areas in the form of two panels hingedly connected in seriatim to one another by way of a connecting panel, wherein: a first discrete area (i) is provided with a plurality of discrete separable, bibulous, pH indicator strips, each strip comprising a non-bleeding rectangular strip, each strip having two unique visually-recognizable areas and a zone thereon which may be gripped by the fingers of the user provided by being impregnated with at least two selected acid-base indicators, said acid-base indicator being visually recognizable as at least one unique color on each of said bibulous pH indicator strip when said bibulous strip is dry and as a different color upon being wetted with water, said different color being dependent on the pH of said water; a second discrete area (ii) is provided with seven distinct rectangular areas, each area including two unique different colors, thereby providing a plurality of color comparison reference standards in a plurality of zones, each zone being of a unique color which corresponds to the color of said water-wetted bibulous pH indicator strip, whereby comparison of the unique color of said pH indicator strip with the unique color of said reference standard provides an indication of the pH of said water, and, by reference to indicia thereon, to indicate which fish are unlikely to be found in the water which wetted said bibulous strip and a third discrete area (iii) is on the back face of said first discrete panel, said back face being imprinted with instructions for the use of said acid monitoring kit to correlate the unique color developed in said bibulous pH indicator strip tp a unique color on said reference standard, to provide an indication of the pH of the water.

14. A kit adapted to assist in the determination of the likely presence of aquatic species in a body of water in dependence upon a determined pH for said body of water, said kit comprising in combination:

first and second base members hingedly connected to one another so as to be relatively foldable between closed and opened conditions; a plurality of discrete, separable, bibulous, pH indicator strips attached to said first base member so as to be covered by said second base member when said first and second base members are in said closed condition thereof, and being exposed when said first and second members are in said opened condition thereof so as to allow a user to separate at least one of said indicator strips from said first member;

each said indicator strip being provided with a pH test region which consists essentially of an acid-base indicator which changes from a normal color when dry to a visually perceptible unique color when wetted with water from said body of water being tested, wherein said unique color is indicative of the pH of the body of water being tested;

a plurality of color comparison reference standards imprinted upon said second member, each said color comparison reference standard corresponding to one possible pH indicative unique color of said wetted indicator strip; and a plurality of information zones each being associated with a respective one of said color comparison reference standards for identifying the likely presence of aquatic species in the body of water being tested in dependence upon the pH of the body of water corresponding to said respective color comparison reference standard, whereby matching the unique color of said wetted indicator strip with one of said color comparison reference standards will allow a user to determine the likely presence of aquatic species in said body of water by virtue of said associated information zones.

15. The kit of claim 14 wherein said bibulous pH indicator strips are non-bleeding rectangular strips.

* * * * *